United States Patent [19]

Kopecek et al.

[11] Patent Number: 5,415,864
[45] Date of Patent: May 16, 1995

[54] COLONIC-TARGETED ORAL DRUG-DOSAGE FORMS BASED ON CROSSLINKED HYDROGELS CONTAINING AZOBONDS AND EXHIBITING PH-DEPENDENT SWELLING

[75] Inventors: Jindrich Kopecek; Sung W. Kim; Helle Brondsted; Pavla Kopeckova, all of Salt Lake City, Utah

[73] Assignee: University of Utah Research Foundation, Salt Lake City, Utah

[21] Appl. No.: 932,914

[22] Filed: Aug. 20, 1992

Related U.S. Application Data

[63] Continuation of Ser. No. 513,267, Apr. 18, 1990, abandoned.

[51] Int. Cl.$^6$ .............................. A61K 9/48; A61F 9/02
[52] U.S. Cl. .................................. 424/436; 424/78.35; 424/438; 424/468; 424/487; 526/306; 526/307
[58] Field of Search .................. 526/306, 307; 424/79, 424/438, 78.31, 468, 487, 451, 436, 78.35

[56] References Cited

U.S. PATENT DOCUMENTS

| | | | |
|---|---|---|---|
| 4,190,716 | 2/1980 | Parkinson et al. | 524/334 |
| 4,432,966 | 2/1984 | Zietoun et al. | |
| 4,489,197 | 12/1984 | Wang et al. | |
| 4,496,553 | 6/1985 | Halskov | |
| 4,663,308 | 5/1987 | Jaffron et al. | 514/150 |
| 4,971,790 | 11/1990 | Magruder et al. | 424/438 |
| 5,078,994 | 1/1992 | Mair | 424/78.31 |

FOREIGN PATENT DOCUMENTS

| | | |
|---|---|---|
| 1172570 | 8/1984 | Canada. |
| WO81/01290 | 3/1981 | European Pat. Off. ............ 526/306 |
| 0123485 | 10/1984 | European Pat. Off.. |
| 0225189 | 6/1987 | European Pat. Off.. |
| 0297184 | 4/1989 | European Pat. Off. ............ 526/306 |
| 2813771 | 10/1979 | Germany. |
| 61-157513 | 7/1986 | Japan ................................. 526/306 |

OTHER PUBLICATIONS

Hydrogels for Medical and Related Applications pp. 37–51 (Refojo) 1975.
"Isomerization . . . Effect" Eisenbach Polymer, 1980 vol. 21 (1175–1179).
Siegel et al. J. of Controlled Release 8 (1988) 179–182.
Porter, *Remington's Pharmaceutical Sciences*, Mack Publishing Co., Easton, Pa, 17th Edition (1985) pp. 1633–1643.

*Primary Examiner*—Thurman K. Page
*Assistant Examiner*—Peter F. Kulkosky
*Attorney, Agent, or Firm*—Morrison & Foerster

[57] ABSTRACT

Colonic-targeted oral drug dosage forms composed of a drug confined within a crosslinked hydrogel that exhibits pH-dependent swelling and is composed of an ionizable comonomer such as acrylic acid, a nonionizable comonomer such as an acrylamide, and a crosslinking agent that contains an aromatic azobond. Selective drug release in the colon occurs by a combination of pH-dependent swelling of the hydrogel and degradation of the hydrogel by enzymatic cleavage of the azobonds by azoreductases.

38 Claims, 7 Drawing Sheets

Swelling of crosslinked copolymers of N, N-dimethylacrylamide with acrylic acid

Swelling of crosslinked copolymers of
N, N-dimethylacrylamide with acrylic acid

Swelling of crosslinked copolymers of N-dimethylacrylamide with acrylic acid

Swelling of crosslinked copolymers of N-(2-Hydroxypropyl)methacrylamide with acrylic acid

COLONIC-TARGETED ORAL DRUG-DOSAGE FORMS BASED ON CROSSLINKED HYDROGELS CONTAINING AZOBONDS AND EXHIBITING PH-DEPENDENT SWELLING

This application is a continuation of application Ser. No. 07/513,267, filed Apr. 18, 1990, now abandoned.

TECHNICAL FIELD

The present invention relates to novel hydrogels that contain aromatic azobonds in the crosslinks and exhibit pH-dependent swelling that are useful for making oral drug dosage forms that release drug selectively in the colon.

BACKGROUND

Various enteric coatings have been used previously to orally administer drugs that are labile in the stomach and/or are targeted at the large intestine. See *Remington's Pharmaceutical Sciences*, Mack Publishing Company, Easton, Pa., 17th Edition (1985), p. 1637.

Several prior patents describe dosage forms for selectively delivering 5-aminosalicylic acid (5-ASA) to the colon. Halskov (U.S. Pat. No. 4,496,553) describes formulations of 5-ASA with conventional enteric carriers (composed of lactose, potato starch, magnesium stearate and cellulose) that are not readily soluble at low pHs. Similarly, Canadian Patent 1,172,570 describes solid dosage forms of 5-ASA that are coated with methacrylic acid-methacrylic acid ester copolymers that are relatively insoluble in gastric fluid but highly soluble at the higher pHs found in the intestinal fluids. Other patents, such as U.S. Pat. Nos. 4,190,176 and 4,489,197, describe conjugating 5-ASA to nonabsorbable aromatic polymers via azobonds that are stable in the stomach but are cleaved enzymatically in the large intestine to release the 5-ASA.

U.S. Pat. No. 4,663,308—which is perhaps the closest art to the present invention—employs high molecular weight polymers of one or more ethylenically unsaturated monomers copolymerized with a divinylazobenzene compound to coat or otherwise entrap drugs that are labile in the stomach, have an undesirable effect in the stomach, or are targeted at the colon. Release of drug occurs via the cleavage of the azobonds by the azoreductases that abound in the colon but are not prevalent in the stomach or small intestine. The patent suggests various acrylic acid esters and amides as well as unsaturated acids as possible monomers. However, the only copolymer exemplified in the patent is a hydroxyethyl-methacrylate (HEMA)-styrene copolymer that contains no ionizable group. Further, the only ionizable group-containing polymer exemplified in the patent is a crosslinked polyacrylic acid. In this regard, drug release from the formulations of the present invention is controlled by a combination of pH-dependent swelling of the copolymer and degradation of the hydrogel via cleavage of the azobonds by the azoreductases in the colon. Further, the copolymers of U.S. Pat. No. 4,663,308 are crosslinked under the gel point (branched) and are thus soluble in organic solvents. In contrast, the copolymers of the present invention are crosslinked beyond the gel point and are insoluble in any solvent.

Siegel et al., *J. Controlled Release* (1988) 8(2):179–182, employs hydrophobic polyamine hydrogels that swell selectively at low pHs to administer drugs orally in a manner that avoids premature release of drug in the oral cavity but permits release in the stomach. Such hydrogels would not be useful for delivering drugs selectively to the colon.

DISCLOSURE OF THE INVENTION

The present invention provides: novel crosslinked hydrogels that undergo pH-dependent swelling and contain azobonds that are enzymatically cleavable by the azoreductases that reside in the colon; oral drug dosage forms composed of such hydrogels that permit selective release of drug in the colon; methods for selectively delivering drugs to the colon employing such oral dosage forms; two processes for making such hydrogels; conjugates of hydrogels which exhibit pH-dependent swelling, and optionally include enzymatically-cleavable azobonds, and amino group-containing drugs that are covalently bound to the hydrogel via an aromatic azobond; and a process for making such conjugates.

The crosslinked hydrogels of the invention are comprised of: (a) at least one ethylenically unsaturated comonomer containing no ionizable group; (b) at least one ethylenically unsaturated comonomer containing one or more ionizable groups; (c) a crosslinking agent containing an aromatic azobond; and (d) optionally a crosslinking agent without aromatic azobonds, said hydrogel being crosslinked beyond the gel point and containing an amount of (b) such that the hydrogel exhibits pH-dependent swelling.

The oral dosage forms of the invention comprise a drug confined within, e.g., dispersed in or encapsulated by, the hydrogel, or bound via aromatic azobonds to the hydrogel.

The method of delivering a drug selectively to the colon of a patient according to the invention comprises confining the drug within the hydrogel and administering the thus-confined drug orally to the patient.

One of the processes for making the above-described hydrogels comprises the steps of: forming a solution of the comonomers ((a) and (b) above), the azobond-containing crosslinking agent ((c) above), and optionally (d); subjecting the solution to crosslinking copolymerization conditions and carrying out the reaction beyond the gel point.

The other process for making the hydrogels comprises: forming a solution of the comonomers and at least one ethylenically unsaturated comonomer having a terminal reactive group; copolymerizing the mixture of the three types of comonomers to form a polymeric precursor; forming a mixture of the polymeric precursor and one or more crosslinking agents containing moieties which can form covalent bonds with the reactive group; and subjecting the mixture to crosslinking conditions and carrying out the crosslinking beyond the gel point.

The drug-hydrogel conjugates of the invention comprise: (a) at least one ethylenically unsaturated comonomer unit containing no ionizable group; (b) at least one ethylenically unsaturated comonomer unit containing an ionizable group; (c) at least one ethylenically unsaturated comonomer unit having a drug covalently bound thereto via an aromatic azobond; and (d) a bifunctional crosslinking agent, said hydrogel being crosslinked beyond the gel point and containing an amount of (b) such that the copolymer exhibits pH-dependent swelling. The crosslinking agent may or may not contain aromatic azobonds or it may be a mixture of an agent that contains an aromatic azobond and an agent that does not contain an azobond.

MODES FOR CARRYING OUT THE INVENTION

A. Definitions

Figure 1:
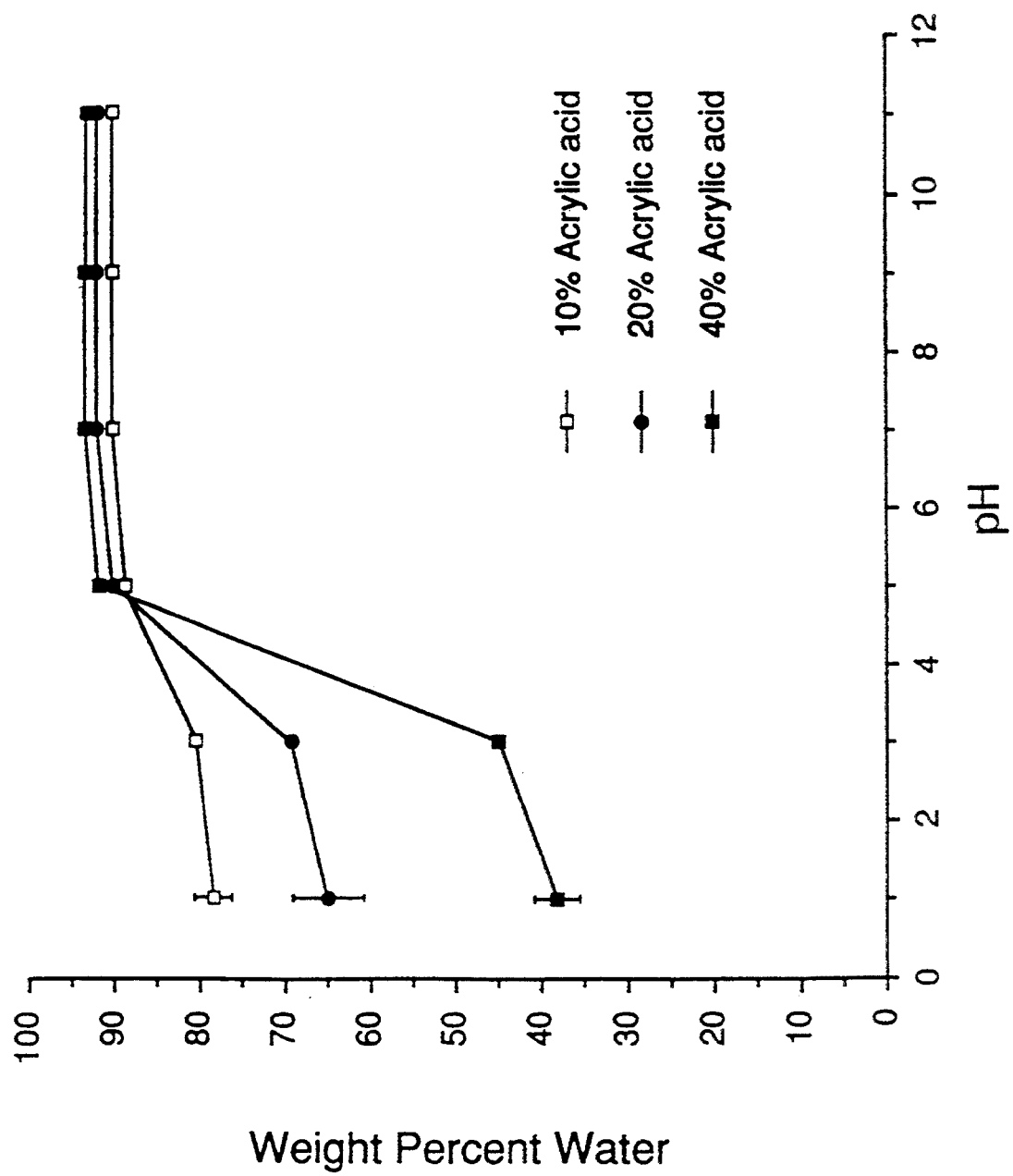
FIGS. 1 to 4 are graphs showing the degree of swelling of various copolymers of the invention as a function of pH.
Figure 2:
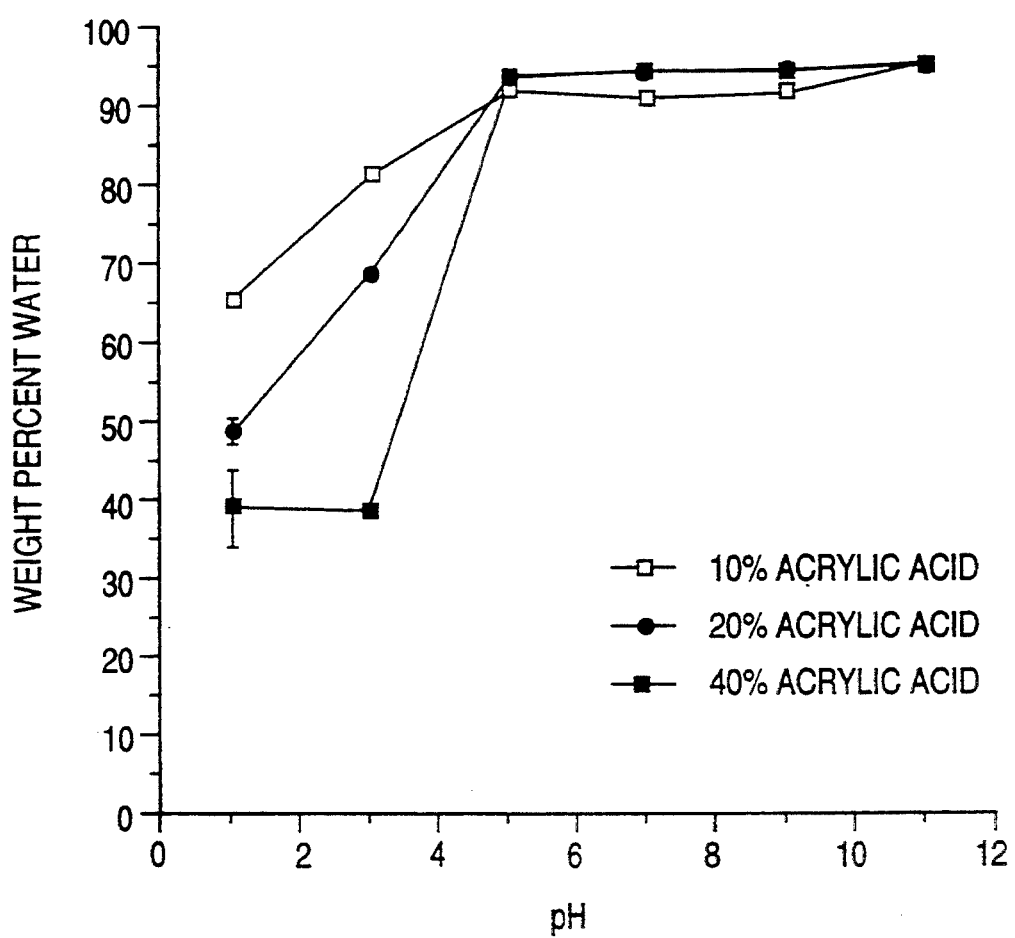
Figure 3:
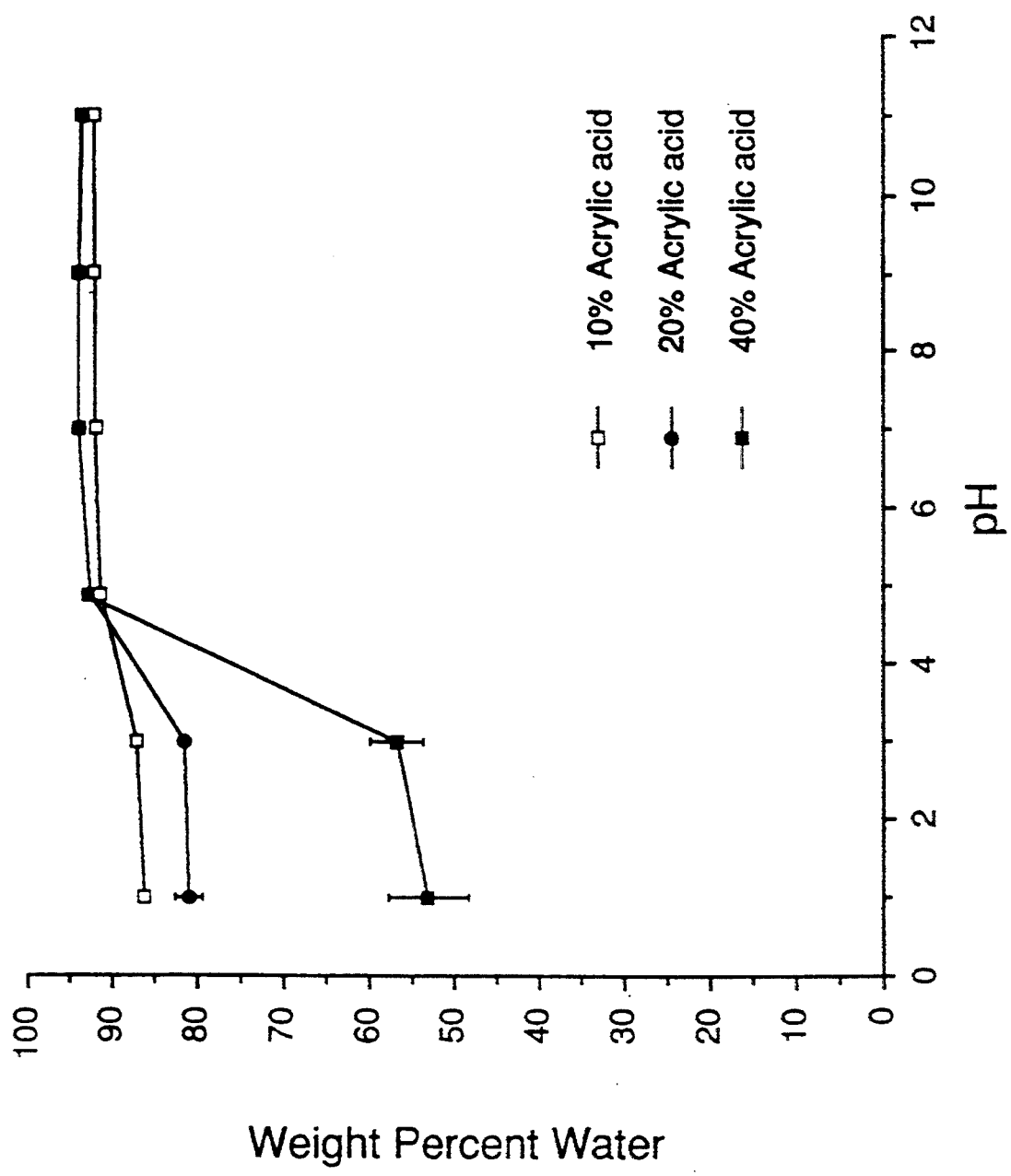
Figure 4:
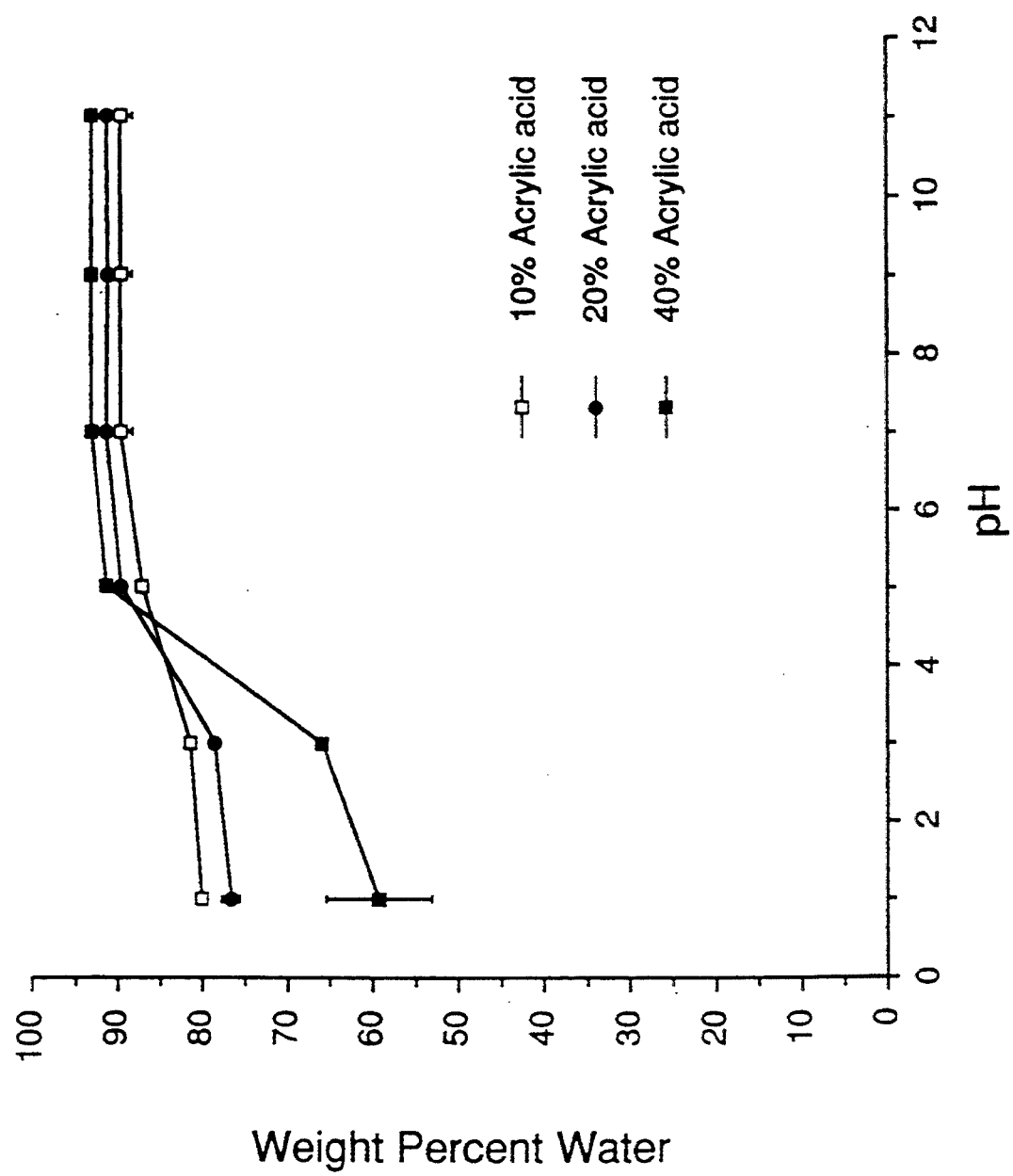

"Ethylenically unsaturated" intends the presence of a carbon-to-carbon double bond ($>C=C<$).

An "ionizable group" is a chemical group that dissociates into charged ions at pHs greater than about 4. Examples of such groups are carboxyl, $SO_3H$, and substituted phenolic groups.

An "aromatic azobond" intends an azo group ($-N=N-$) with each nitrogen atom bound directly to a nuclear carbon atom of an aromatic ring, e.g., a benzene ring.

The "gel point" of a crosslinking reaction is that point in the crosslinking reaction at which the reaction mixture loses fluidity. The products of reactions carried beyond the gel point are infinite network polymers that are insoluble in all solvents. See Odian, G., *Principles of Polymerization*, 2nd ed., Wiley-Interscience; ISBN 047105146-2; pp. 117-127.

As used herein "pH-dependent swelling" intends a hydrogel that imbibes a substantially greater amount of water at the pH found in the colon (above about 4) than at the pH found in the stomach (below about 4). "Substantially greater" will normally intend at least about 10% more water, more usually at least about 30% more water.

The word "selective" used to describe the release or delivery of drug from the invention dosage form intends that the substantial proportion (usually at least about 10%, more usually 50%) of the drug released from the dosage form is released in the colon as opposed to the upper regions of the gastrointestinal tract.

B. Composition of Hydrogels

The invention hydrogels are composed of at least two types of ethylenically unsaturated monomers and a crosslinking agent that contains an aromatic azobond.

One of the comonomer types contains no ionizable group. These comonomers are preferably acrylamides or acrylic acid esters of the formulas

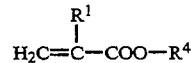

where $R^1$ is H, methyl or ethyl, and $R^2$ and $R^3$ are individually H, alkyl of 1 to 8 carbon atoms (methyl-octyl), hydroxyalkyl of 1-12 carbon atoms and 1-3 hydroxy groups, or hydroxyalkoxyalkyl of 2-12 carbon atoms and 1-3 hydroxy groups

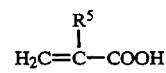

where $R^1$ is as above and $R^4$ is alkyl of 1 to 12 carbon atoms (methyl-dodecyl), hydroxyalkyl of 1 to 12 carbon atoms and 1 to 3 hydroxy groups, or hydroxyalkoxyalkyl of 2 to 12 carbon atoms and 1 to 3 hydroxy groups. The alkyl groups of greater than 2 carbon atoms that are represented by $R^2$, $R^3$ and $R^4$ may be linear or branched Other comonomers of the non-ionizable type are styrene, N-vinyl pyrollidone, acrylonitrile, N-acryloyl morpholine, methacrylonitrile, vinylacetate, and alpha-methylstyrene.

The other type of comonomer contains an ionizable group. These comonomers are preferably unsaturated acids of the formula

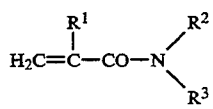

where $R^5$ is alkyl of 1 to 4 carbon atoms.

Other comonomers that contain an ionizable group include N-methylacryloylglycine, N-methacryloyl epsilon-aminocaproic acid, 2-sulfoethylmethacrylate, N-methacryloylundecanoic acid, maleic anhydride, crotonic acid, and similar monomers.

When the hydrogels are formed by first synthesizing a polymeric precursor and then crosslinking the precursor, a third comonomer type having a reactive group, such as an active ester group, will be included to provide reactive sites for crosslinking. Preferred comonomers of this third type are carboxylic esters of the formula:

where $R^6$ is hydrogen, methyl or ethyl, $R^7$ is a residue of p-nitrophenol, 2,3,5-trichlorophenol, 8-hydroxyquinoline, N-hydroxysuccinimide, N-hydroxyphthalimide, or any carbonyl activating group, n is 0 or an integer from 1 to 3 inclusive, and x is 1 when n is from 1 to 3 and an integer from 2 to 10, inclusive, when n is 0; and the functional groups of the bifunctional crosslinking agent are amino groups or hydroxy groups.

Other reactive comonomers are N-methacryloylated oligopeptides whose terminal COOH group is activated by $R^7$ or chlorides of unsaturated acids.

The crosslinking agent contains an aromatic azobond that is cleaved by the azoreductases that are present in the colon. (As indicated above, the hydrogels may be crosslinked with a mixture of such crosslinking agents and agents that do not contain aromatic azobonds.) Depending upon the manner in which the copolymer is synthesized (i.e., by crosslinking copolymerization or by crosslinking of a polymeric precursor), the crosslinking agent will either also contain two ethylenically unsaturated bonds or be bifunctional (have groups, such as amino or hydroxy groups, preferably located at the ends of the molecule, that will react with the reactive groups, such as the reactive ester groups, in the precursor).

The azobond-containing crosslinking agents that may be used in the crosslinking copolymerization process are

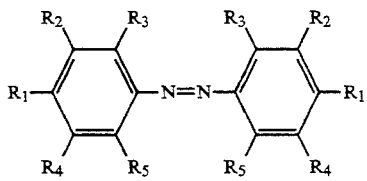

where $R_1$ is

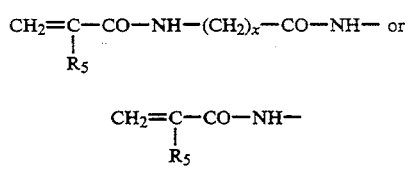

where x is an integer from 1 to 12 inclusive, and $R_6$ is H, methyl or ethyl, and $R_2$, $R_3$, $R_4$ and $R_5$ are individually H, $CH_3$, $OCH_3$, Br, Cl, F, I, $NO_2$, CN or $C(O)CH_3$.

Preferred crosslinking agents for use in the crosslinking copolymerization synthesis are 4,4'-di(methacryloylamino)azobenzene, 4,4'-di(N-methacryloyl-epsilon-aminocaproyl)aminoazobenzene, 4,4'-di(methacryloylamino)-3,3',5,5'tetrachloroazobenzene, 4,4'-di(-methacryloylglycinamidoazobenzene; and di(methacryloylamino)-3,3',5,5'tetranitroazobenzene.

Preferred crosslinking agents of the bifunctional type are compounds of the formula

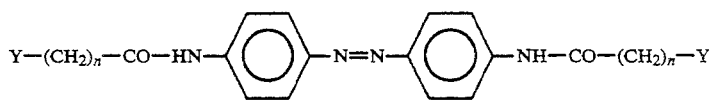

where n is an integer from 1 to 12 inclusive, and Y is a functional group, such as $NH_2$ or OH, that reacts with the reactive group in the polymeric precursor to form a covalent bond.

The extent of pH-dependent swelling exhibited by the hydrogels will depend on (a) the amount of ionizable comonomer in the copolymer (b) the structure and compositional ratios of all monomers and (c) the network density (degree of crosslinking) of the copolymer. (Swelling also depends on the nature of the drug as discussed infra.) In general, the extent of pH-dependent swelling increases with increasing amounts of ionizable monomer and decreasing degree of crosslinking. A very important factor is the hydrophobic-hydrophilic balance in the hydrogel structure, since it influences the difference in the degrees of swelling at pH 2 and pH 7.

Normally the mol % of ionizable comonomer in the copolymer will be in the range of about 1 to 90, preferably 20 to 70. Correlatively, the mol % of nonionizable comonomer in the copolymer will normally be in the range of 10 to 98.95, preferably 30 to 80. The mol % of third monomer in copolymer made via polymeric precursors will usually be in the range of 0.1 to 50, preferably 3 to 20. The amount of crosslinking agent incorporated in the copolymers will be sufficient to insure that the crosslinking reaction occurs beyond the gel point.

Normally about 0.05 to 15 mol % crosslinking agent is incorporated, preferably 0.1 to 1 mol %.

C. Synthesis of Hydrogels

As indicated previously, the hydrogels may be made by crosslinking copolymerization or by first forming a polymeric precursor containing pendant reactive groups and crosslinking the precursor using a bifunctional crosslinking agent.

In the crosslinking copolymerization reaction the comonomers and crosslinking agents are dissolved in a suitable solvent such as dimethylsulfoxide (DMSO), dimethylformamide (DMF), $DMSO/H_2O$, or ethanol (EtOH). The copolymerization can be performed without solvent if desired. The reaction is carried out in the absence of oxygen and is initiated by adding a free radical initiator to the reaction mixture. The reaction conditions are such that the reaction proceeds beyond the gel point.

In the other reaction scheme the ionizable comonomer, nonionizable comonomer and the comonomer containing a reactive group are dissolved in a solvent such as those described above. The copolymerization of the three types of comonomers is carried out in the absence of oxygen, and is initiated by adding a free radical initiator to the solution. A 3 to 20% by weight solution of the resulting polymeric precursor containing side chains terminated by reactive groups in a solvent is combined with the bifunctional aromatic azobond-containing crosslinking agent and optionally a crosslinking agent without azobonds is also added. Crosslinks are formed via reactions between the reactive groups on the precursor and the functional groups on the crosslinking agent.

D. Formulation of Hydrogel and Drug

The drugs that are advantageously administered via the dosage forms of the invention are drugs that would be destroyed by the environments of the stomach/small intestine, have an irritating or other undesirable effect on the tissues of the upper gastrointestinal tract, or are intended to locally treat conditions within the colon or colonic tissue. Systemically acting drugs that are delivered via these dosage forms must be capable of being absorbed into circulation through the mucosal lining of the colon. Examples of drugs that may be delivered advantageously via this invention are peptide or protein drugs such as insulin, calcitonin, angiotensin, cyclosporin, vasopressin, and somatostatin.

The drugs may be formulated with the hydrogels by dispersing them in the hydrogels or by enclosing or encapsulating them in a film or membrane of the hydrogel. Dispersions are made by mixing the drug with the solution of monomers/polymeric precursor and then forming the hydrogel by crosslinking as described above. Alternatively a body of the hydrogel may be soaked in a solution or dispersion of the drug which swells the hydrogel and the body then dried (solution sorption technique). The drug-hydrogel dispersions may be cut or otherwise shaped into a body containing the desired unit dose of drug. The amount of drug administered may be varied by varying the concentration of drug in the solution or dispersion, the solvent used to create the solution or dispersion, and the volume of the drug-hydrogel body. The drugs may be enclosed in a film or membrane of the copolymer by forming the copolymer into a film or membrane, placing a desired amount of drug between two pieces of the film/membrane and sealing the edges of the pieces. In this manner a container whose walls are made of the copolymer and whose lumen contains a unit dose of drug are prepared. Alternatively, drug tablets, capsules or microspheres may be coated with the polymeric precursor and the precursor crosslinked in situ using the procedure described above. Drug tablets, capsules or microspheres may also be coated with the hydrogel using a latex-type suspension of the hydrogel (e.g., a suspension of fine particles in a swelling agent/dispersant). As will be appreciated by those of skill in the art, various additives and carriers may be included in the drug formulation, if desired.

The dosage forms of the invention are administered orally to the animal or human to be treated with the drug. Because the azoaromatic crosslinks of the hydrogel are substantially stable in the stomach and small intestine and because of the low degree of swelling of the hydrogel in the acidic conditions of the stomach no or a limited amount of drug is released in the stomach. Depending upon the drug involved and the degree of swelling exhibited by the hydrogel, drug may or may not be released within the small intestine. The particular hydrogel used with a given drug will depend upon the properties of the drug (molecular weight and water solubility) and the desired pattern of drug release. In general, drugs with low water solubilities and high molecular weights will be released more slowly from a given hydrogel. Accordingly, hydrogels having a higher degree of swelling may be required to achieve desired release of high molecular weight, water insoluble drugs. Correlatively, it may be desirable to use hydrogels having low degrees of swelling for drugs that have low molecular weights and/or that act as osmotic agents. In any event, the degradation of the hydrogels by the microbial azoreductases of the gastrointestinal tract depends strongly on the equilibrium degree of swelling of the hydrogel. By knowing the diffusion rate of drugs through the hydrogel, the transit time of the dosage form through the tract and the rate of enzymatic degradation, adjustment of copolymer composition, drug loading, and dosage form geometry can be made to obtain a desired drug release pattern.

E. Hydrogel-Drug Conjugates

Drugs with aromatic amino groups such as 5-ASA and N-(4-aminobenzenesulfonyl)-N'-butylurea may also be covalently bound to the hydrogels of the invention via aromatic azobonds or in a similar manner to hydrogels that exhibit pH-dependent swelling but lack aromatic azobonds. Such conjugates are composed of: the ionizable comonomer; the nonionizable comonomer; a third ethylenically unsaturated comonomer having a reactive group and which when incorporated into the copolymer has the drug covalently bound thereto via an aromatic azobond; and a bifunctional crosslinking agent. The conjugate is crosslinked beyond the gel point and contains sufficient ionizable comonomer to exhibit pH-dependent swelling. The bifunctional crosslinking agent may or may not contain an aromatic azobond or may consist of a mixture of a crosslinking agent that contains an aromatic azobond and a crosslinking agent that does not contain an aromatic azobond. In such conjugates drug release occurs via cleavage of the azobond between the drug and hydrogel by azoreductases. Such enzymatic degradation is, in turn, controlled by the pH-dependent swelling of the hydrogel.

These conjugates may be made by a variation of the polymeric precursor mode for making the invention hydrogels. The precursor is first formed as described above. It is then reacted with the bifunctional crosslinking agent and a derivative of the drug that contains a functional group that will react with the reactive group of the precursor and which has the drug coupled to the remainder of the derivative by an aromatic azobond. For instance, in the case of 5-ASA, 4-[(4-hydroxy-3-carboxyphenylazo]-N-(2-aminoethyl)benzamide could be used as the 5-ASA derivative. Examples of bifunctional crosslinking agents that do not contain an azobond are the alkylenediamines, e.g., hexylenediamine.

The amount of drug incorporated into these conjugates will depend upon the amount of the reactive group-containing monomer in the precursor and the relative amounts and reactivities of the drug derivatives and bifunctional crosslinking agent. By knowing the amount of drug per unit weight of conjugate an appropriate amount of conjugate may be administered orally to deliver the desired dose of drug to the colon.

F. Examples

The following examples further illustrate the various aspects of the invention. They are not intended to limit the invention in any manner.

1. Preparation of hydrogels by crosslinking copolymerization 1.341 ml N,N-dimethylacrylamide, 0.338 g N-t-butylacrylamide, 0.728 ml acrylic acid and 0.0925 g N,N-di(methacryloylamino)azobenzene was dissolved in 5.85 ml DMSO by heating in a waterbath (about 50° C.) to dissolve all solid compounds. Then the mixture was bubbled with nitrogen for 30 min and 12 ul t-butylperoxyoctoate was added as initiator. The mixture was polymerized between glass plates separated by a rubber ring to obtain membranes. The polymerization took place at 80° C. for 48 hr in a thermostated waterbath. The composition (mol %) of the resulting hydrogel was: 49.0% N,N-dimethylacrylamide; 40% acrylic acid; 10% N-t-butylacrylamide; and 1.0% 4,4'-di(methacryloylamino)azobenzene.

In a similar manner two other hydrogels were prepared with 10% and 20% acrylic acid and correspondingly greater amount of N,N-dimethylacrylamide.

In addition corresponding sets of three hydrogels containing 10%, 20% and 40% acrylic acid respectively with acrylamide, N-methylacrylamide, or N-(2-hydroxypropyl) methacrylamide in place of N,N-dimethylacrylamide were prepared.

Also a set of four other hydrogels were prepared using varying amounts of crosslinking agent. The compositions of these copolymers were: 40% acrylic acid; 10% N-t-butylacrylamide, 49-49.9% N,N-dimethylacrylamide and 0.1%, 0.2%, 0.5%, and 1.0% 4,4'-di(methacryloylamino) azobenzene.

2. Evaluation of pH-dependent swelling of hydrogels

Three disks 10–15 mm in diameter were cut from each hydrogel membrane of Example 1. The equilibrium degree of swelling was measured using a citrate-borate-phosphate/HCl universal buffer system at pH 3, 5, 7, 9 and 11. Swelling at pH 1 was measured in a HCl/KCl buffer. The ionic strength was adjusted with sodium chloride to 0.16 in all buffer solutions. The swelling was measured at 37° C. After determination of the weight of the swollen gel, the gels were washed in water and dried in a vacuum oven at 40°–50° C. for 48 hr. The results of these tests are shown graphically in FIGS. 1–5.

As shown in FIGS. 1–4 the pH-dependent swelling is strongly dependent upon the amount of ionizable comonomer (acrylic acid) present. Swelling was also dependent upon the structure of the nonionizable comonomer, but to a lesser degree.

Figure 5:
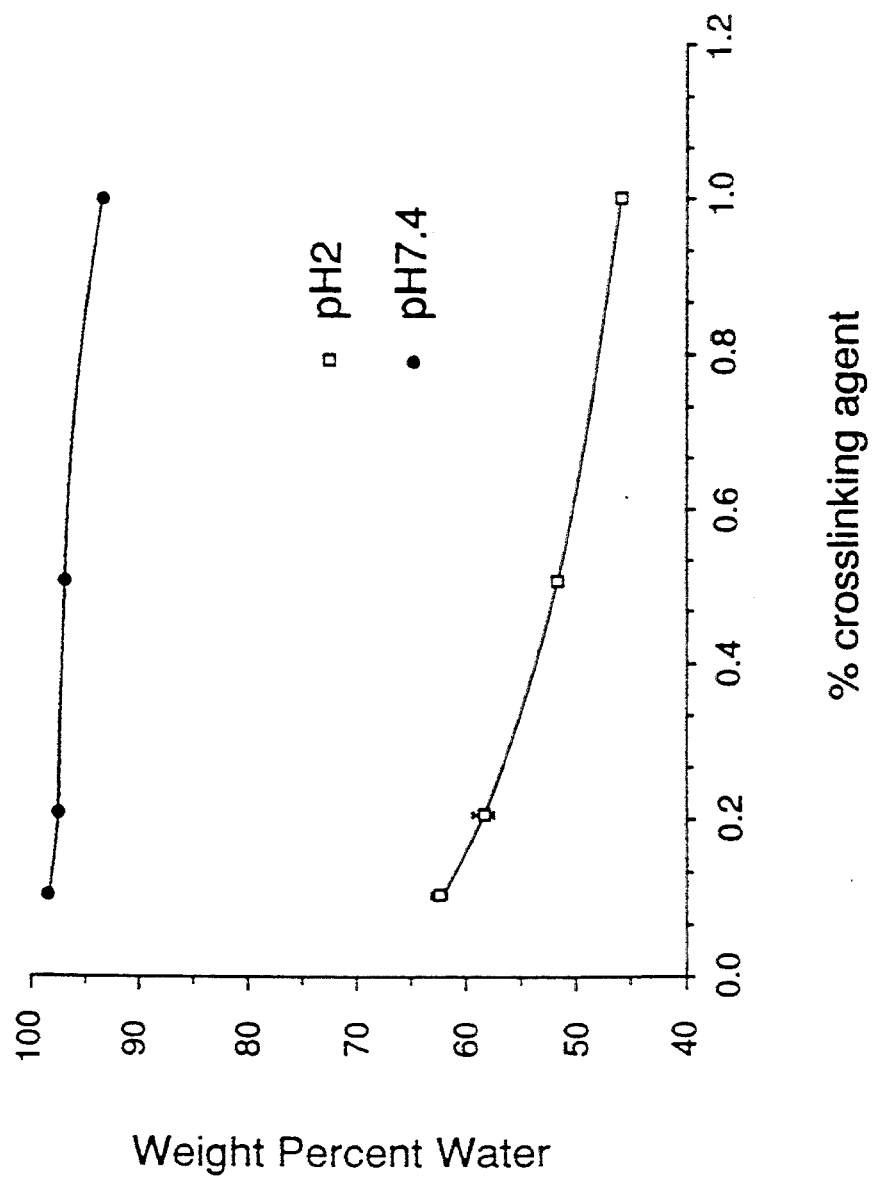
FIG. 5 is a graph showing the degree of swelling of copolymers of this invention at two different pHs as a function of the amount of crosslinking agent in the copolymer.

FIG. 5 shows that the degree of crosslinking has a significant effect upon swelling at low pHs but much less effect at higher pHs.

3. Evaluation of permeability of hydrogels

Diffusion experiments were done in a two compartment diffusion cell. The cell was thermostated at 3° C. The cell volumes were 2.3 ml and the area available for diffusion was 0.785 cm$^2$. A preswollen hydrogel membrane was mounted between the two compartments using a silicone rubber ring to protect the membrane. The donor compartment was then filled with a solution of drug (radioactive) in buffer and the receiver compartment was filled with buffer. At regular time intervals samples were taken from the receiver side and replaced with buffer solution, and the samples counted in a scintillation counter.

The permeability of insulin through a membrane composed of 40% acrylic acid, 10% N-t-butylacrylamide, 49% N,N-dimethylacrylamide and 1% N,N-di(-methacryloylamino)azobenzene (all in mol %) was determined to be $3.3 \times 10^{-8}$ cm$^2$/s at pH 2 and at pH 7.4 to be $4.7 \times 10^{-7}$ cm$^2$/s.

4. Degradability of hydrogels in vitro

Degradation of the gels was investigated using cell free extract (CFE) prepared from rat cecum contents. The method was modified from the method described by Brown (Brown, J., *Applied and Environmental Microbiology*, May 1981, 1283–1286). The cell free extract was prepared by suspending 1 g rat cecum contents in 10 ml potassium phosphate buffer 0.01M, pH 7.4. The microflora cells were sonically disrupted for 15 min at 0°–4° C., then the mixture was filtered through glasswool and centrifuged at 13,000 rpm at 0°–4° C. The supernatant is then isolated and kept in freezer until use. For the degradation experiments the gel was left in the following solution: 4 ml CFE, 2 ml phosphate buffer 0.1M pH 7.4, 0.47 mg/ml glucose-6-phosphate, 0.38 mg/ml NADP and 0.11 mg/ml benzyl-viologen. This was bubbled with nitrogen to obtain anaerobic conditions and 12 U glucose-6-phosphate dehydrogenase was added to initiate the reaction.

After 90 hr of degradation of a gel composed of 40% acrylic acid, 10% N-t-butylacrylamide, 49% N,N-dimethylacrylamide and 1% N,N-di(methacryloylamino)azobenzene (Gel B) 0.5 mm in thickness and 0.5 cm in diameter, the color of the gel changed from yellow to colorless, indicating cleavage of aromatic azo bonds. The degradation was evaluated by an increase in degree of swelling. Gel A containing 0.2% of crosslinking agent and Gel C containing 2% of crosslinking agent were also evaluated.

Three gels of the above-described structure were evaluated to determine the relationship between the degree of swelling and degradability in vitro. They differed in the network density and in their equilibrium degree of swelling.

Gel A: initial degree of swelling 56.5% (swollen weight/dry weight). After degradation the swelling increased to 103.3%, i.e., increase by 83%. Gel B: initial 19.6%; after degradation 29.5%; increase 51%. Gel C: initial 14.8%; after degradation 18.0%; increase 22%. The size of the swollen gels during degradation changed accordingly. Similar results can be obtained by changing the structure of gels by varying the content of ionizable comonomers. These results demonstrate the possibility of regulating the rate of degradation of the hydrogels by tailor-making their structure.

5. In vivo degradation of hydrogels

A hydrogel disc 1 mm in height and 4 mm in diameter was preswollen in PBS pH 7.4 at 37° C. The gel was placed in a nylon bag (6×6 mm) and implanted in the cecum of a 200 g male rat (Sprague-Dawley) anaesthetized with ether. This was done by incision through the midline of the abdominal muscle opening the peritoneal cavity. The cecum was found right underneath the incision and was carefully pulled out of the body. A small cut was made in the upper part of the cecum and with a pair of ring-forceps, the bag containing the hydrogel was placed inside the cecum and secured with silk through the opening. The opening in the cecum was tied off to prevent leakage and was carefully washed clean and inspected for any leakage. Then the cecum was inserted back into the peritoneal cavity and the incisions were sutured closed. The rat woke up shortly thereafter. The animal was allowed rat chow and water ad libitum. After two days the rat was sacrificed and the bag recovered from the cecum. The gel was washed in buffer and swollen to equilibrium and weighed. After washing with water, the gel was dried and the dry weight measured.

Figure 6:
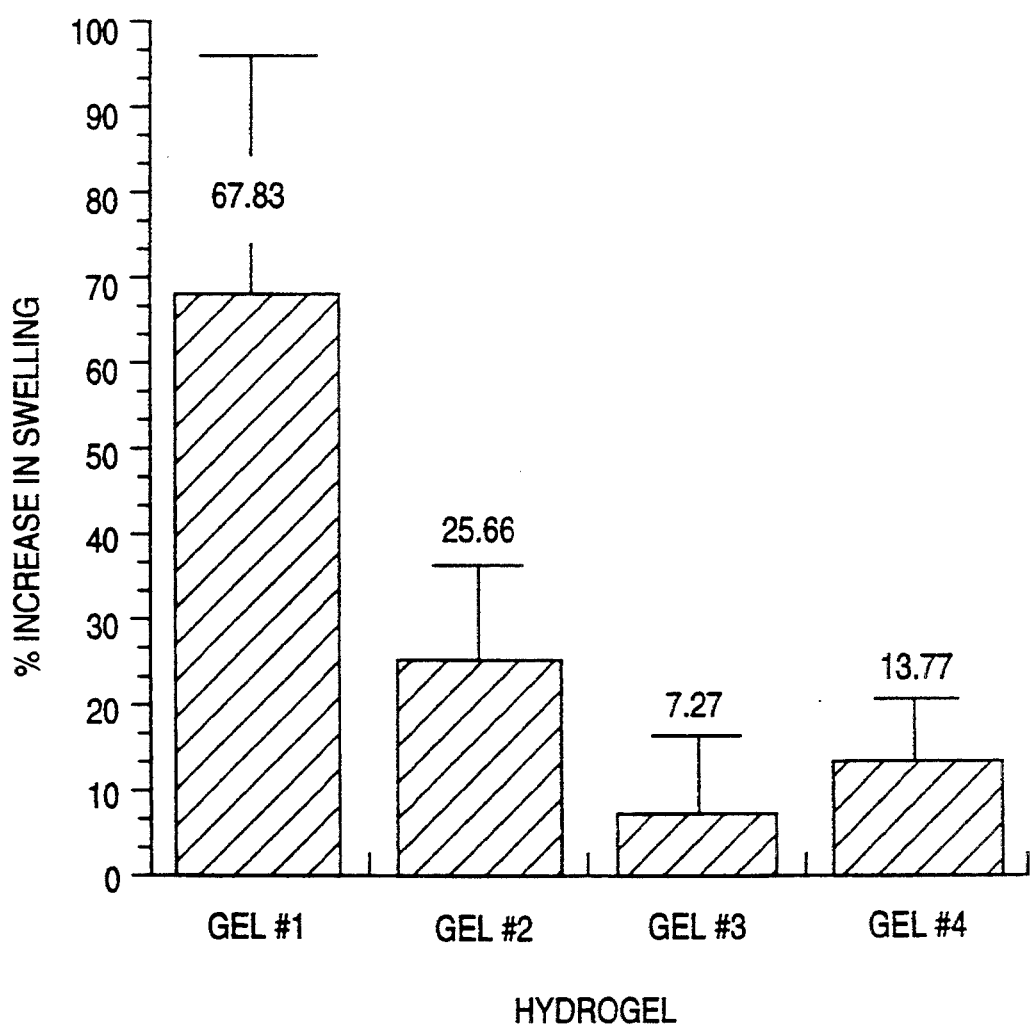
FIG. 6 is a graph showing the in vivo degradability of various copolymers of the invention.

The compositions of the hydrogels tested were as follows: Gel #1: 49.8% N,N-dimethylacrylamide, 40% acrylic acid, 10% N-t-butylacrylamide and 0.2% 4,4'-di(methacryloylamino)azobenzene. Gel #2: 49.5% N,N-dimethylacrylamide, 40% acrylic acid, 10% N-tert.butylacrylamide and 0.5% 4,4'-di(methacryloylamino)azobenzene. Gel #3: 49.0% N,N-dimethylacrylamide, 40% acrylic acid, 10% N-tert.butylacrylamide and 1.0% 4,4'-di(methacryloylamino)azobenzene. Gel #4: 19.0% N,N-dimethylacrylamide, 70% acrylic acid, 10% N-t-butylacrylamide and 1.0% 4,4'-di(methacryloylamino)azobenzene. The visible appearance of some samples were found to change from dark yellow to colorless. This was more pronounced for gels with lower crosslinking densities. The increase in swelling was evaluated as the percent increase in water content (i.e., weight of swollen gel after degradation—weight of swollen gel before degradation)×100%/(weight of swollen gel before degradation). The results of these tests are shown in FIG. 6.

6. Hydrogels prepared by crosslinking copolymerization of butylacrylate, acrylic acid and 4,4-(methacryloylamino)azobenzene A) Synthesis of Hydrogels Hydrogels of acrylic acid and butyl acrylate crosslinked with di(4,4'-methacryloylamino)azobenzene were prepared by radical copolymerization with benzoylperoxide as the initiator. Solutions of monomers (1 g), crosslinker (1 mol % with respect to the monomeric mixture), initiator (0.1 mol % with respect to monomeric mixture) in 2 ml of DMSO were placed in a 5 ml ampule, sparged 10 min with nitrogen, sealed and polymerized 50 h at 80° C. in a thermostated water bath. After polymerization the ampule was broken and the hydrogel washed in ethanol (3 days), water (1–2 days) and buffer (2 weeks) at 25° C.

B) Evaluation of Swelling

Figure 7:
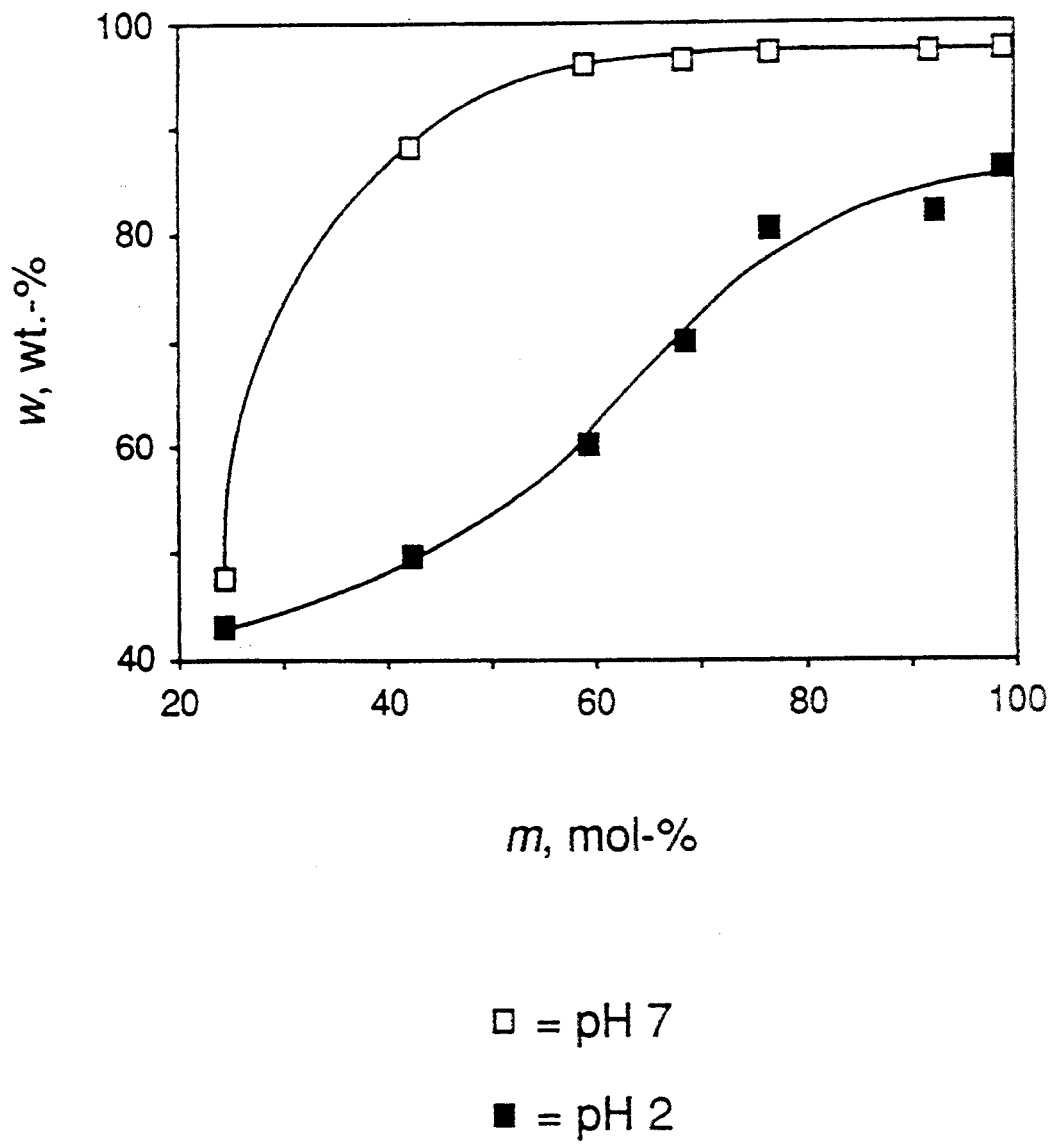
FIG. 7 is a graph showing the dependence of equilibrium water content (w) in hydrogels prepared by copolymerization of butylacrylate/acrylic acid and 4,4'-di(-methacryloylamino) azobenzene on the content of acrylic acid (m) at pH 2 and pH 7 (preparation of hydrogels is described in Example 6).

The degrees of swelling of the hydrogels were determined gravimetrically as the content of water in equilibrium swollen samples at pH 2 and 7, 37° C. and with 0.32 mol dm$^{-3}$ osmolarity, and are shown in FIG. 7.

7. Degradable hydrogels prepared by crosslinking of polymeric precursors

A) Preparation of polymeric precursors

N-(2-hydroxypropyl)methacrylamide and N-methacryloylglycylglycine p-nitrophenyl ester (mol ratio 4:1) were copolymerized in a mixture of acetone and dimethyl sulfoxide (95:5, v/v) for 40 h at 50° C. The total concentration of monomers was 12.5 %-wt and the concentration of azobisisobutyronitrile was 0.6 %-wt. After polymerization the solution was rotoevaporated to a viscous liquid and precipitated into an excess of acetone/diethyl ether (3:2). The p-nitrophenoxy (ONp) group content as determined by UV spectrophotometry was 25.0 mol %.

B) Crosslinking

One-tenth of a gram of polymeric precursor containing $3 \times 10^{-4}$ mol ONp groups was dissolved in 0.8 ml of dimethyl sulfoxide (DMSO). A solution of 6.5 mg ($1.5 \times 10^{-5}$ mol) of N,N'-di(epsilon-aminocaproyl)-4,4'-diaminoazobenzene in 0.13 ml of DMSO was added and stirred briefly. Within seconds a biodegradable hydrogel was formed. Changing the concentration of polymeric precursor, the amount of ONp groups, the ratio of ONp:NH$_2$ groups, it is possible to control the time of gelation and the crosslinking density.

8. Preparation of a hydrogel containing 5-amino salicylic acid (5-ASA) bound via azoaromatic degradable bonds and degradable crosslinks A) Preparation of polymeric precursor containing carboxylic groups:

N-(2-hydroxypropyl)methacrylamide, N-methacryloylglycylglycine p-nitrophenyl ester and acrylic acid (mol ratio 7:2:1) were copolymerized in a mixture of acetone and DMSO (90:10, v/v) for 40 h at 55° C. The total concentration of monomers was 11%-wt and concentration of azobisisobutyronitrile was 0.7%-wt. After polymerization the solution was rotoevaporated to a viscous liquid and precipitated into an excess of acetone/diethyl ether (3:1, v/v). The content of ONp groups as determined by UV spectrophotometry was 23.5 mol %.

B) Synthesis of 4-(4-hydroxy-3-carboxyphenyl azo)-N-(2-aminoethyl)benzamide hydrochloride:

4.13 g ($2.5 \times 10$ mol) of ethyl p-aminobenzoate was dissolved in 13 ml of diluted (1:1) HCl and cooled to 4° C. A solution of 1.9 g ($2.75 \times 10^{-2}$ mol) NaNO$_2$ in 3.5 ml H$_2$O was added and the reaction allowed to proceed for 10 min. The excess of HNO$_2$ was decomposed by the addition of 0.25 g (2.5 mmol) of sulfamic acid.

The coupling of salicylic acid to the diazonium salt prepared as above was performed as follows: to the cooled solution of the salt 3.45 g ($2.75 \times 10^{-2}$ mol) of salicylic acid in 20% Na$_2$CO$_3$ were added. The pH of the reaction mixture was adjusted to 9-10 and the mixture was reacted 1 h under cooling and stirring. The sodium salt of ethyl-4-(4-hydroxy-3-carboxyphenylazo)benzoate which precipitated during the reaction was filtered off, recrystallized from C$_2$H$_5$OH/H$_2$O (1:7) . The free acid was isolated by dissolving the sodium salt in C$_2$H$_5$OH/H$_2$O, acidification of conc. HCl and crystallization. Overall yield was 5 4 g (68%). M.p. 216°-217° C. $\Sigma^{358} = 2.6 \times 10^4$ l·mol·cm (C$_2$H$_5$OH)·C$_{16}$H$_{14}$N$_2$O$_5$ (314,3) Calc. C 61.15, H 4.49, N 8.91; Found C 60.86, H 4.50, N 8.75. IR (KBr) 1020 ($\gamma_s$ C—O—C); 1220 ($\gamma_{as}$ C—O—C); 1300 ($\gamma$C—O); 1690 ($\gamma$C=O acid); 1720 ($\gamma$C=O ester); 3180 ($\gamma$OH carboxyl); 3420 cm$^{-1}$ ($\gamma$OH).

Two grams (6.4 mmol) of ethyl-4-(4-hydroxy-3-carboxyphenylazo)benzoate was dissolved in 10 ml of ethylenediamine and refluxed 48 h under N$_2$ atmosphere. The solution was rotoevaporated and residual oil was solidified by treatment with cold methanol, filtered and washed with methanol and diethyl ether. The product, 4(4-hydroxy-3-carboxyphenylazo)-N-(2-aminoethyl)benzamide, was isolated as the hydrochloride after dissolution in HCl/CH$_3$OH, and crystallization from CH$_3$OH. Yield 1.2 g (50%). M.p. 240° C. (decomp). $\Sigma^{359} = 2.5 \times 10^4$ l·mol·cm$^{-1}$ (PBS, pH 7.4). C$_{16}$H$_{17}$N$_4$O$_4$Cl (364.8). Calc. C 52.68, H 4.70, N 15.36, C19.72. Found C 52.10, H 4.84, N 15.19, Cl 10.49. IR (KBr) 1300 (amide III); 1550 (amide II); 1655 (amide I); 2350–2750 ($\gamma$NH$_2^+$); 3480 cm$^{-1}$ ($\gamma$NH).

C) Conjugate Drug Binding and Crosslinking:

One-tenth gram of polymeric precursor containing $2.8 \times 10^{-4}$ mol of ONp groups was dissolved in 0.7 ml DMSO. A solution of 0.018 g of 4-(4-hydroxy-3-carboxyphenylazo)-N-(2-aminoethyl)benzamide was added under stirring. After 30 min a solution of N,N'-(epsilon-aminocaproyl)-4,4'-diaminoazobenzene (crosslinking agent; 6.1 mg; $1.4 \times 10^{-5}$ mol) in 0.14 ml of DMSO was added and the mixture briefly stirred. A gel was formed which contained ionizable carboxylic groups and side-chains terminating in a low molecular weight drug (5-ASA) bound via azoaromatic bonds and cleavable (azobond containing) crosslinks.

9. Preparation and evaluation of a hydrogel containing 5-ASA bound via degradable bonds and nondegradable crosslinks B) Crosslinking:

One-tenth gram of polymeric precursor (prepared as described in Example 8) containing $2.8 \times 10$ mol of ONp groups was dissolved in 0.7 ml of DMSO. A solution of 18 mg ($5.6 \times 10^{-5}$ mol) of 4-(4-hydroxy-3-carboxyphenyl azo)-N-(2-aminoethyl)benzamide in 0.1 ml of DMSO was added under stirring. After 30 min a solution of 1,6-diaminohexane (1.6 mg; $1.4 \times 10$ mol) in 0.15 ml of DMSO was added and briefly stirred. A gel was formed which contained ionizable COOH groups; side-chains terminating in 5-ASA bound via a degradable bond and nondegradable crosslinks.

Thirty-five hundreds gram of swollen hydrogel ($20 \times 20 \times 3$ mm) was equilibrated in 2 ml of cell-free extract (isolated from rat cecum) containing $8.3 \times 10^{-4}$M glucose-6-phosphate; $2.5 \times 10^{-4}$M of beta-NADP and $1.3 \times 10^{-4}$M of benzyl viologen. The mixture was bubbled with nitrogen for 2 hours and then the degradation was initiated by addition of glucose-6-phosphate (1 unit/ml). During incubation (24 hours at 37° C) the gel gradually changed color from yellow to colorless, indicating the release of 5-ASA. The color change started from the margins of the hydrogel and proceeded towards the center.

10. Preparation of a hydrogel containing 5-ASA bound via degradable bonds and two types of crosslinks: degradable and nondegradable One-tenth gram of polymeric precursor (prepared as described in Example 8) containing $2.8 \times 10^{-4}$ mol of ONp groups was dissolved in 0.7 ml of DMSO. A solution of 18 mg of 4-(4-hydroxy-3-carboxyphenylazo)-N-(2-aminoethyl)benzamide in 0.1 ml DMSO was added under stirring. After 30 min a solution of two crosslinking agents: 3.1 mg ($7 \times 10^{-6}$ mol) of N,N'-di(epsilon-aminocaproyl)-4,4-diaminoazobenzene and 8 mg ($7\times10^{-6}$ mol) of 1,6-diaminohexane in 0.15 ml of DMSO was added and shortly vigorously stirred. A gel was formed which contained ionizable COOH groups; a low molecular weight drug (5-ASA) bound via degradable bonds; degradable and nondegradable crosslinks. The pH-dependent swelling is controlled by the content of ionizable groups. After arrival in the colon, degradable crosslinks will be cleaved by azoreductases. Consequently, the swelling degree will further increase. The release of the low molecular weight drug can be controlled by the detailed structure of the hydrogel.

11. Release of insulin from hydrogel in vitro

A piece of gel (13 mm in diameter in swollen state, 3 mm in thickness) with the composition: 0.2% 4,4'-di(-methacryloylamino)azobenzene, 40% acrylic acid, 10% N-tert.butylacrylamide, and 49.8% N,N-dimethylacrylamide prepared according to Example 1, was soaked in a $^{14}$C-labeled insulin solution (2 mg/ml) at pH 11 for 15 h. The gel was dried at room temperature for 40 h and quickly washed with buffer pH 2 to remove the drug adsorbed on the surface. After that, the gel was immersed in buffer pH 2, then in a mixture of cell-free extract (CFE), isolated from rat cecum, and cofactors (6 ml containing 4 ml CFE, 2 ml phosphate buffer 0.1M pH 7.4, 0.47 mg/ml glucose-6-phosphate, 0.38 mg/ml NADP, and 0.11 mg/ml benzyl viologen). The mixture was bubbled with nitrogen and the degradation was initiated by addition of 12 U glucose-6-phosphate-dehydrogenase. Release of insulin was observed during the whole period of observation (5 h) as detected by monitoring the increase in radioactivity of the supernatant.

Modifications of the above-described modes for carrying out the invention that are obvious to those of skill in polymer chemistry, pharmaceutical formulation, drug delivery, and related fields are intended to be within the scope of the following claims.

We claim:

1. A crosslinked hydrogel comprised of:
   (a) at least one ethylenically unsaturated comonomer containing no ionizable group;
   (b) at least one ethylenically unsaturated comonomer containing an ionizable group; and
   (c) a crosslinking agent containing an aromatic azo-bond,
   said copolymer being crosslinked beyond the gel point and containing an amount of (b) such that the hydrogel exhibits pH-dependent swelling wherein the hydrogen imbibes at least about 10% more water at the pH found in the human colon than at the pH found in the human stomach.

2. The hydrogel of claim 1 wherein
   (a) is selected from the group consisting of
   (i) acrylamides of the formula:

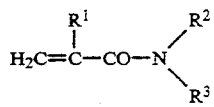

where $R^1$ is hydrogen, methyl or ethyl, and $R^2$ and $R^3$ are hydrogen, alkyl of 1 to 8 carbon atoms, hydroxylalkyl of 1 to 12 carbon atoms and 1 to 3 hydroxy groups, or hydroxyalkoxyalkyl of 2 to 12 carbon atoms and 1 to 3 hydroxy groups;
   (ii) acrylates of the formula:

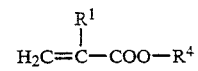

where $R^1$ is as defined previously and $R^4$ is alkyl of 1 to 12 carbon atoms, hydroxyalkyl of 1 to 12 carbon atoms and 1 to 3 hydroxy groups, or hydroxyalkoxyalkyl of 2 to 12 carbon atoms and 1 to 3 hydroxy groups,
   (iii) styrene,
   (iv) N-vinylpyrollidone,
   (v) acrylonitrile,
   (vi) methacrylonitrile,
   (vii) N-acryloylmorphine,
   (viii) vinylacetate, or
   (ix) alpha-methylstyrene, and
   (b) is selected from the group consisting of
   (i) an unsaturated acid of the formula:

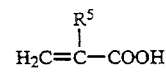

where $R^5$ is hydrogen or alkyl of 1 to 4 carbon atoms, and
   (ii) N-methylacryloylglycine,
   (iii) N-methacryloyl epsilon-aminocaproic acid,
   (iv) α-sulfoethylmethacrylate,
   (v) N-methacryloylundecanoic acid,
   (vi) maleic anhydride, and
   (vii) crotonic acid.

3. The hydrogel of claim 2 wherein the crosslinking agent is of the formula:

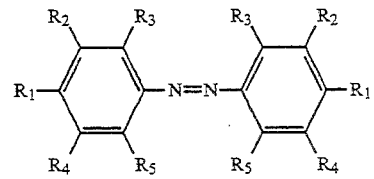

where $R_1$ is

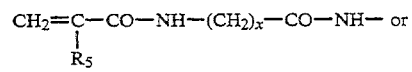

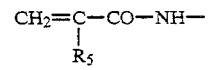

where x is an integer from 1 to 12 inclusive, and $R_6$ is H, methyl or ethyl and $R_2$, $R_3$, $R_4$ and $R_5$ are individually H, $CH_3$, $OCH_3$, Br, Cl, F, I, $NO_2$, CN or $C(O)CH_3$.

4. The hydrogel of claim 2 wherein the crosslinking agent is 4,4'-di(methacryloylamino)azobenzene, 4,4'-di(N-methacryloyl-epsilon-aminocaproyl)aminoazobenzene, or 4,4'-di(methacryloylamino)-3,3',5,5'-tetrachloroazobenzene.

5. The hydrogel of claim 1 wherein (a) constitutes about 10 to about 99 mol % of the hydrogel and (b) constitutes about 1 to about 90 mol % of the hydrogel and the crosslinking agent constitutes about 0.05 to about 15% of the hydrogel.

6. The hydrogel of claim 1 further comprised of (d) a crosslinking agent that does not contain an aromatic azobond.

7. An oral drug dosage form that releases drug selectively in the colon comprising a drug confined within the crosslinked hydrogel copolymer of claim 1.

8. The oral drug dosage form of claim 7 wherein the drug is dispersed homogeneously in the hydrogel.

9. The oral drug dosage form of claim 7 wherein the hydrogel defines a wall enclosing a lumen and the drug is contained within the lumen.

10. The oral drug dosage form of claim 7 wherein the drug is coated with the hydrogel.

11. The oral dosage form of claim 7 wherein the hydrogel defines the wall of an enclosed capsule or pouch and the drug is contained within the capsule or pouch.

12. An oral drug dosage form that releases drug selectively in the colon comprising a drug confined within the crosslinked hydrogel copolymer of claim 2.

13. An oral drug dosage form that releases drug selectively in the colon comprising a drug confined within the crosslinked hydrogel copolymer of claim 3.

14. An oral drug dosage form that releases drug selectively in the colon comprising a drug confined within the crosslinked hydrogel copolymer of claim 4.

15. An oral drug dosage form that releases drug selectively in the colon comprising a drug confined within the crosslinked hydrogel copolymer of claim 5.

16. An oral drug dosage form that releases drug selectively in the colon comprising a drug confined within the crosslinked hydrogel copolymer of claim 6.

17. A method of delivering a drug selectively to the colon of a patient comprising:
(a) confining the drug within the crosslinked hydrogel of claim 1; and
(b) administering the thus-confined drug orally to the patient.

18. A process for making the hydrogel of claim comprising the steps of:
forming a solution of (a), (b), and (c) wherein (c) contains at least two ethylenically unsaturated bonds in addition to said aromatic azobond; and
subjecting the solution to crosslinking copolymerization conditions wherein the crosslinking copolymerization is carried out beyond the gel point.

19. The process of claim 18 wherein (a) constitutes about 10 to 99 mol % of the total monomers and (b) constitutes about 1 to 90 mol % of the total monomers.

20. The process of claim 18 wherein
(a) is selected from the group consisting of
(i) acrylamides of the formula:

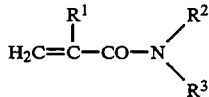

where $R^1$ is hydrogen, methyl or ethyl, and $R^2$ and $R^3$ are hydrogen, alkyl of 1 to 8 carbon atoms, hydroxylalkyl of 1 to 12 carbon atoms and 1 to 3 hydroxy groups, or hydroxyalkoxyalkyl of 2 to 12 carbon atoms and 1 to 3 hydroxy groups;
(ii) acrylates of the formula:

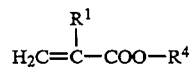

where $R^1$ is as defined previously and $R^4$ is alkyl of 1 to 12 carbon atoms, hydroxyalkyl of 1 to 12 carbon atoms and 1 to 3 hydroxy groups, or hydroxyalkoxyalkyl of 2 to 12 carbon atoms and 1 to 3 hydroxy groups,
(iii) styrene,
(iv) N-vinylpyrollidone,
(v) acrylonitrile,
(vi) methacrylonitrile,
(vii) N-acryloylmorphine,
(viii) vinylacetate, or
(ix) alpha-methylstyrene, and
(b) is selected from the group consisting of
(i) an unsaturated acid of the formula:

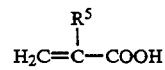

where $R^5$ is hydrogen or alkyl of 1 to 4 carbon atoms, and
(ii) N-methylacryloylglycine,
(iii) N-methacryloyl epsilon-aminocaproic acid,
(iv) α-sulfoethylmethacrylate,
(v) N-methacryloylundecanoic acid,
(vi) maleic anhydride, and
(vii) crotonic acid.

21. The process of claim 20 wherein the crosslinking agent is a compound of the formula:

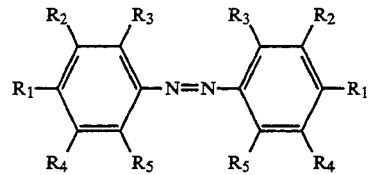

where $R_1$ is

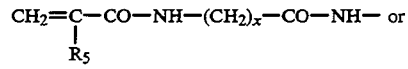

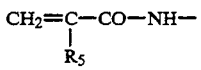

where x is an integer from 1 to 12 inclusive, and $R_6$ is H, methyl or ethyl and $R_2$, $R_3$, $R_4$ and $R_5$ are individually H, $CH_3$, $OCH_3$, Br, Cl, F, I, $NO_2$, CN or $C(O)CH_3$.

22. A process for making the hydrogel of claim 1 comprising the steps of:
forming a solution of (a), (b), and at least one ethylenically unsaturated comonomer having a terminal reactive group;
subjecting the solution to copolymerization conditions whereby a soluble polymeric precursor is formed which contains side chains terminated by said reactive group;
forming a mixture of said precursor and (c) wherein (c) is a bifunctional crosslinking agent; and subjecting the mixture to crosslinking conditions wherein the crosslinking is carried out beyond the gel point.

23. A process for making the hydrogel of claim 6 comprising the steps of:
forming a solution of (a) and (b), and at least one ethylenically unsaturated comonomer having a terminal reactive group;
subjecting the solution to copolymerization conditions whereby a soluble polymeric precursor is formed which contains side chains terminated by said reactive group;
forming a mixture of said precursor and (c) and (d) wherein (c) and (d) are bifunctional crosslinking agents; and
subjecting the mixture to crosslinking conditions wherein the crosslinking is carried out beyond the gel point.

24. The process of claim 22 wherein
(a) is selected from the group consisting of
(i) acrylamides of the formula:

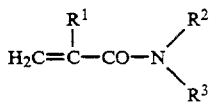

where $R^1$ is hydrogen, methyl or ethyl, and $R^2$ and $R^3$ are hydrogen, alkyl of 1 to 8 carbon atoms, hydroxylalkyl of 1 to 12 carbon atoms and 1 to 3 hydroxy groups, or hydroxyalkoxyalkyl of 2 to 12 carbon atoms and 1 to 3 hydroxy groups;
(ii) acrylates of the formula:

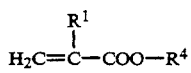

where $R^1$ is as defined previously and $R^4$ is alkyl of 1 to carbon atoms, hydroxyalkyl of 1 to 12 carbon atoms and 1 to 3 hydroxy groups, or hydroxyalkoxyalkyl of 2 to 12 carbon atoms and 1 to 3 hydroxy groups,
(iii) styrene,
(iv) N-vinylpyrollidone,
(v) acrylonitrile,
(vi) methacrylonitrile,
(vii) N-acryloylmorphine
(viii) vinylacetate, or
(ix) alpha-methylstyrene, and
(b) is selected from the group consisting of
(i) an unsaturated acid of the formula:

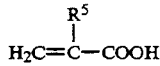

where $R^5$ is hydrogen or alkyl of 1 to 4 carbon atoms, and
(ii) N-methylacryloylglycine,
(iii) N-methacryloyl epsilon-aminocaproic acid,
(iv) α-sulfoethylmethacrylate,
(v) N-methacryloylundecanoic acid,
(vi) maleic anhydride, and
(vii) crotonic acid.

25. The process of claim 24 wherein the bifunctional crosslinking agent is of the formula:

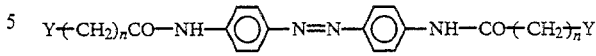

where Y is amino or hydroxy and n is an integer from 1 to inclusive.

26. The hydrogel of claim 1 including an amino-containing drug covalently bound to the copolymer via an aromatic azobond.

27. The copolymer of claim 26 wherein the drug is 5-aminosalicylic acid.

28. A crosslinked hydrogel copolymer-drug conjugate useful for delivering the drug selectively to the colon comprised of:
(a) at least one ethylenically unsaturated comonomer unit containing no ionizable group;
(b) at least one ethylenically unsaturated comonomer unit containing an ionizable group;
(c) at least one ethylenically unsaturated comonomer unit having a drug covalently bound thereto in an aromatic azobond; and
(d) a bifunctional crosslinking agent, said copolymer being crosslinked at the gel point and containing an amount of (a) such that the copolymer exhibits pH-dependent swelling wherein the hydrogel imbibes at least about 10% more water at the pH found in the human colon than at the pH found in the human stomach.

29. The hydrogel of claim 28 wherein the bifunctional crosslinking agent contains an aromatic azobond.

30. The hydrogel of claim 28 wherein the bifunctional crosslinking agent does not contain an aromatic azobond.

31. The hydrogel of claim 28 wherein the bifunctional crosslinking agent is a mixture of a crosslinking agent containing an aromatic azobond and a crosslinking agent that does not contain an aromatic azobond.

32. A method of delivering a drug selectively to the colon of a patient comprising administering the hydrogel of claim 28 orally to the patient.

33. The hydrogel of claim 1 wherein the ionizable group is carboxyl.

34. The hydrogel of claim 1 wherein
(a) is selected from the group consisting of N,N-dimethylacryladmie, N-t-butylacrylamide, acrylamide, N-methylacrylamide, N-(2-hydroxypropyl)methacrylamide, and butylacrylate,
(b) is acrylic acid, and
(c) is N,N-di-(methylacryloylamino)azobenzene.

35. The hydrogel of claim 18 wherein
(a) is selected from the group consisting of N,N-dimethylacryladmie, N-t-butylacrylamide, acrylamide, N-methylacrylamide, N-(2-hydroxypropyl)methacrylamide, and butylacrylate,
(b) is acrylic acid, and
(c) is N,N-di-(methylacryloylamino)azobenzene.

36. The hydrogel of claim 1 wherein the hydrogel includes a third comonomer that has a reactive group prior to crosslinking and the crosslinking agent has prior to crosslinking at least two functional groups that are capable of reacting with the reactive group of the third comonomer.

37. The hydrogel of claim 36 wherein the third comonomer has the formula:

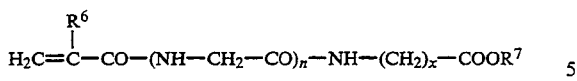

where $R^6$ is hydrogen, methyl, or ethyl, $R^7$ is a residue of a carbonyl activating group, n is 0 or an integer from 1 to 3 inclusive, and X is 1 when n is from 1 to 3 and an integer from 2 to 10 inclusive when n is 0 and the functional groups are amino or hydroxy.

38. The hydrogel of claim 37 wherein
(a) is selected from the group consisting of
(i) acrylamides of the formula:

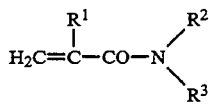

where $R^1$ is hydrogen, methyl or ethyl, and $R^2$ and $R^3$ are hydrogen, alkyl of 1 to 8 carbon atoms, hydroxylalkyl of 1 to 12 carbon atoms and 1 to 3 hydroxy groups, or hydroxyalkoxyalkyl of 2 to 12 carbon atoms and 1 to 3 hydroxy groups;
(ii) acrylates of the formula:

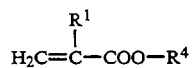

where $R^1$ is as defined previously and $R^4$ is alkyl of 1 to 12 carbon atoms, hydroxyalkyl of 1 to 12 carbon atoms and 1 to 3 hydroxy groups, or hydroxyalkoxyalkyl of 2 to 12 carbon atoms and 1 to 3 hydroxy groups,
(iii) styrene,
(iv) N-vinylpyrollidone,
(v) acrylonitrile,
(vi) methacrylonitrile,
(vii) N-acryloylmorphine,
(viii) vinylacetate, or
(ix) alpha-methylstyrene, and
(b) is selected from the group consisting of
(i) an unsaturated acid of the formula:

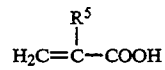

where $R^5$ is hydrogen or alkyl of 1 to 4 carbon atoms, and
(ii) N-methylacryloylglycine,
(iii) N-methacryloyl epsilon-aminocaproic acid,
(iv) 2-sulfoethylmethcrylate,
(v) N-methacryloylundecanoic acid,
(vi) maleic anhydride, and
(vii) crotonic acid.

* * * * *